US008206684B2

(12) United States Patent
McCutcheon et al.

(10) Patent No.: US 8,206,684 B2
(45) Date of Patent: Jun. 26, 2012

(54) METHODS AND DEVICES FOR BLOCKING FLOW THROUGH COLLATERAL PATHWAYS IN THE LUNG

(75) Inventors: John McCutcheon, Menlo Park, CA (US); Antony J. Fields, San Francisco, CA (US); David Peter Shaw, Christchurch (NZ)

(73) Assignee: Pulmonx Corporation, Redwood City, CA (US)

( * ) Notice: Subject to any disclaimer, the term of this patent is extended or adjusted under 35 U.S.C. 154(b) by 840 days.

(21) Appl. No.: 11/067,025

(22) Filed: Feb. 25, 2005

(65) Prior Publication Data

US 2005/0196344 A1 Sep. 8, 2005

Related U.S. Application Data

(60) Provisional application No. 60/548,791, filed on Feb. 27, 2004.

(51) Int. Cl.
*A61N 33/44* (2006.01)
*A61M 11/00* (2006.01)
(52) U.S. Cl. .................... 424/1.25; 128/200.23
(58) Field of Classification Search .................. None
See application file for complete search history.

(56) References Cited

U.S. PATENT DOCUMENTS

| | | | |
|---|---|---|---|
| 2,981,254 A | 4/1961 | Vanderbilt | 128/350 |
| 3,657,744 A | 4/1972 | Ersek | 128/334 |
| 3,667,069 A | 6/1972 | Blackshear et al. | 3/1 |
| 3,788,327 A | 1/1974 | Donowitz et al. | 128/350 |
| 3,874,388 A | 4/1975 | King et al. | 128/334 |
| 4,014,318 A | 3/1977 | Dockum et al. | 128/1 |
| 4,086,665 A | 5/1978 | Poirier | 623/1 |
| 4,212,463 A | 7/1980 | Repinski et al. | |
| 4,250,873 A | 2/1981 | Bonnet | 600/104 |
| 4,302,854 A | 12/1981 | Runge | 3/1.7 |
| 4,477,930 A | 10/1984 | Totten et al. | 3/1.5 |
| 4,710,192 A | 12/1987 | Liotta et al. | 623/1 |
| 4,732,152 A | 3/1988 | Wallsten et al. | 128/343 |
| 4,759,758 A | 7/1988 | Gabbay | 623/2 |
| 4,774,942 A | 10/1988 | Moellers | 128/205.24 |
| 4,795,449 A | 1/1989 | Schneider et al. | 604/329 |
| 4,808,183 A | 2/1989 | Panje | 623/9 |
| 4,819,664 A | 4/1989 | Nazari | 128/207.15 |
| 4,830,003 A | 5/1989 | Wolff et al. | 128/343 |
| 4,832,680 A | 5/1989 | Haber et al. | 600/31 |
| 4,846,836 A | 7/1989 | Reich | 623/11 |
| 4,850,999 A | 7/1989 | Planck | 623/1 |
| 4,852,568 A | 8/1989 | Kensey | 128/325 |
| 4,877,025 A | 10/1989 | Hanson | 128/107.16 |
| 4,879,998 A | 11/1989 | Moellers | 128/205.24 |
| 4,934,999 A | 6/1990 | Bader | 600/29 |
| 4,968,294 A | 11/1990 | Salama | 600/30 |
| 4,990,151 A | 2/1991 | Wallstén | 606/108 |
| 5,061,274 A | 10/1991 | Kensey | 606/213 |
| 5,116,360 A | 5/1992 | Pinchuk et al. | 623/1 |
| 5,116,564 A | 5/1992 | Jansen et al. | 264/255 |
| 5,123,919 A | 6/1992 | Sauter et al. | 623/2 |
| 5,151,105 A | 9/1992 | Kwan-Gett | 623/1 |
| 5,158,548 A | 10/1992 | Lau et al. | 604/96 |
| 5,161,524 A | 11/1992 | Evans | 128/203.15 |
| 5,306,234 A | 4/1994 | Johnson | 604/49 |
| 5,352,240 A | 10/1994 | Ross | 623/2 |
| 5,358,518 A | 10/1994 | Camilli | 623/2 |
| 5,366,478 A | 11/1994 | Brinkerhoff et al. | 660/213 |
| 5,382,261 A | 1/1995 | Palmaz | 606/158 |
| 5,392,775 A | 2/1995 | Adkins et al. | 128/207.16 |
| 5,409,019 A | 4/1995 | Wilk | 128/898 |
| 5,411,507 A | 5/1995 | Heckele | 606/108 |
| 5,411,552 A | 5/1995 | Andersen et al. | 623/2 |
| 5,413,599 A | 5/1995 | Imachi et al. | 623/2 |
| 5,417,226 A | 5/1995 | Juma | 128/885 |
| 5,445,626 A | 8/1995 | Gigante | 604/349 |
| 5,453,090 A | 9/1995 | Martinez et al. | 604/53 |
| 5,486,154 A | 1/1996 | Kelleher | 600/104 |
| 5,499,995 A | 3/1996 | Teirstein | 606/192 |
| 5,500,014 A | 3/1996 | Quijano et al. | 623/2 |
| 5,522,881 A | 6/1996 | Lentz | 623/1 |
| 5,562,608 A | 10/1996 | Sekins et al. | 604/20 |
| 5,645,519 A | 7/1997 | Lee et al. | 600/114 |
| 5,645,565 A | 7/1997 | Rudd et al. | 606/213 |

(Continued)

FOREIGN PATENT DOCUMENTS

EP 0621 015 10/1994

(Continued)

OTHER PUBLICATIONS

Gonzalez et al., Should patients undergoing a bronchoscopy be sedated? Acta Anaesthesiol Scand. Apr. 2003;47(4):411-5.*
Cohn et al., Novel reverse thermoresponsive injectable poly(ether carbonates)s, 2003 Kluwer Academic Publishers (pp. 175-180).*
Cetti, E.J., Moore, A.J., Geddes, D.M., "Collateral Ventilation," Thorax 2006;61:371-373 (abstract).*
Al Jishi et al., "Selective Bronchial Occlusion for Treatment of Bullous Interstitial Emphysema and Bronchopleural Fistula." *J. of Pediatric Surgery*, 29:1545-1547, 1994.
Article: "Autocath® 100—Nonsurgical, Intraurethral Bladder Control Device for Incontinent and Retentive Women—Dr. Kulisz's Development".
Derwent citing Russian Patent No. RU 2140211, published Oct. 27, 1999, for: "Method of surgical treatment of patients with pathology of respiratory organs complicated with pulmonary hemorrhages".
Derwent citing Soviet Union Patent No. SU 852-321, published Jul. 8, 1981, for: "Treatment for acute pulmonary and pleural disease in children—by pneumo-abcessotomy simultaneous with occlusion of affected lung part".

(Continued)

*Primary Examiner* — Michael G Hartley
*Assistant Examiner* — Nabila Ebrahim
(74) *Attorney, Agent, or Firm* — Wilson Sonsini Goodrich & Rosati (57) ABSTRACT

Disclosed is a method of regulating fluid flow for a targeted lung region. The method comprises injecting a therapeutic agent into the targeted lung region. The therapeutic agent induces a reaction in lung tissue of the targeted lung region or in a collateral pathway to the lung region to reduce collateral fluid flow into the targeted lung region. In one aspect, the method additionally comprises deploying a bronchial isolation device in the direct pathway to regulate fluid flow to the targeted lung region through the direct pathway. The therapeutic agent can comprise, for example, a sclerosing agent that induces a reaction that causes sclerosis in the lung tissue.

5 Claims, 7 Drawing Sheets

U.S. PATENT DOCUMENTS

| | | | |
|---|---|---|---|
| 5,649,906 A | 7/1997 | Gory et al. | 606/108 |
| 5,660,175 A | 8/1997 | Dayal | 128/207.15 |
| 5,662,713 A | 9/1997 | Andersen et al. | 623/12 |
| 5,683,451 A | 11/1997 | Lenker et al. | 623/1 |
| 5,697,968 A | 12/1997 | Rogers et al. | 623/1 |
| 5,755,770 A | 5/1998 | Ravenscroft | 623/1 |
| 5,800,339 A | 9/1998 | Salama | 600/29 |
| 5,803,080 A | 9/1998 | Freitag | 128/207.14 |
| 5,824,037 A | 10/1998 | Fogarty et al. | 623/1 |
| 5,840,081 A | 11/1998 | Andersen et al. | 623/2 |
| 5,843,158 A | 12/1998 | Lenker et al. | 623/1 |
| 5,851,232 A | 12/1998 | Lois | 623/1 |
| 5,855,587 A | 1/1999 | Hyon et al. | 606/188 |
| 5,855,597 A | 1/1999 | Jayaraman | 623/1 |
| 5,855,601 A | 1/1999 | Bessler et al. | 623/2 |
| 5,868,779 A | 2/1999 | Ruiz | 606/194 |
| 5,891,195 A | 4/1999 | Klostermeyre et al. | 623/2 |
| 5,910,144 A | 6/1999 | Hayashi | 606/108 |
| 5,944,738 A | 8/1999 | Amplatz et al. | 606/213 |
| 5,947,997 A | 9/1999 | Pavcnik et al. | 606/213 |
| 5,954,765 A | 9/1999 | Ruiz | 623/1 |
| 5,954,766 A | 9/1999 | Zadno-Azizi et al. | 623/1.24 |
| 5,957,949 A | 9/1999 | Leonhardt et al. | 606/194 |
| 5,976,174 A | 11/1999 | Ruiz | 606/213 |
| 5,980,455 A | 11/1999 | Daniel et al. | 600/235 |
| 5,984,965 A | 11/1999 | Knapp et al. | 623/1 |
| 5,989,288 A | 11/1999 | Pintauro et al. | 600/30 |
| 6,007,575 A | 12/1999 | Samuels | 623/1 |
| 6,009,614 A | 1/2000 | Morales | 29/516 |
| 6,020,380 A | 2/2000 | Killian | 514/570 |
| 6,022,312 A | 2/2000 | Chaussy et al. | 600/29 |
| 6,027,508 A | 2/2000 | Ren et al. | 606/108 |
| 6,027,525 A | 2/2000 | Suh et al. | 623/1 |
| 6,051,022 A | 4/2000 | Cai et al. | 623/2 |
| 6,068,635 A | 5/2000 | Gianotti | 606/108 |
| 6,068,638 A | 5/2000 | Makower | 606/159 |
| 6,077,291 A | 6/2000 | Das | 606/213 |
| 6,083,255 A | 7/2000 | Laufer et al. | 607/96 |
| 6,123,663 A | 9/2000 | Rebuffat | 600/37 |
| 6,135,729 A | 10/2000 | Aber | 417/420 |
| 6,135,991 A | 10/2000 | Muni et al. | 604/509 |
| 6,141,855 A | 11/2000 | Morales | 29/516 |
| 6,162,245 A | 12/2000 | Jayaraman | 623/1.15 |
| 6,168,614 B1 | 1/2001 | Andersen et al. | 623/1 |
| 6,174,323 B1 | 1/2001 | Biggs et al. | 606/232 |
| 6,183,520 B1 | 2/2001 | Pintauro et al. | 623/23.64 |
| 6,190,381 B1 | 2/2001 | Olsen et al. | 606/32 |
| 6,200,333 B1 | 3/2001 | Laufer | 607/96 |
| 6,206,918 B1 | 3/2001 | Campbell et al. | 623/2.32 |
| 6,234,996 B1 | 5/2001 | Bagaoisan et al. | 604/97.01 |
| 6,240,615 B1 | 6/2001 | Kimes et al. | 29/516 |
| 6,245,102 B1 | 6/2001 | Jayaraman | 623/1.15 |
| 6,247,471 B1 | 6/2001 | Bower et al. | 128/205.21 |
| 6,258,100 B1 | 7/2001 | Alferness et al. | 606/108 |
| 6,270,527 B1 | 8/2001 | Campbell et al. | 623/2.18 |
| 6,280,464 B1 | 8/2001 | Hayashi | 623/1.11 |
| 6,287,290 B1 | 9/2001 | Perkins et al. | 604/516 |
| 6,293,951 B1 | 9/2001 | Alferness et al. | 606/108 |
| 6,302,893 B1 | 10/2001 | Limon et al. | 606/10 |
| 6,312,407 B1 | 11/2001 | Zadno-Azizi et al. | 604/103.03 |
| 6,325,777 B1 | 12/2001 | Zadno-Azizi et al. | 604/97.01 |
| 6,325,778 B1 | 12/2001 | Zadno-Azizi et al. | 604/99.02 |
| 6,327,772 B1 | 12/2001 | Zadno-Azizi et al. | 29/557 |
| 6,328,689 B1 | 12/2001 | Gonzalez | 600/37 |
| 6,355,014 B1 | 3/2002 | Zadno-Azizi et al. | 604/99.02 |
| 6,398,775 B1 | 6/2002 | Perkins et al. | 604/514 |
| 6,402,754 B1 | 6/2002 | Gonzalez | 606/69 |
| 6,416,554 B1 | 7/2002 | Alferness et al. | 623/23.65 |
| 6,458,076 B1 | 10/2002 | Pruitt | 600/146 |
| 6,485,407 B2 | 11/2002 | Alferness et al. | 600/37 |
| 6,491,706 B1 | 12/2002 | Alferness et al. | 606/157 |
| 6,493,589 B1 | 12/2002 | Medhkour et al. | 607/99 |
| 6,510,846 B1 | 1/2003 | O'Rourke | 128/200.21 |
| 6,527,761 B1 | 3/2003 | Soltesz et al. | 604/516 |
| 6,558,318 B1 | 5/2003 | Daniel et al. | 600/213 |
| 6,592,594 B2 | 7/2003 | Rimbaugh et al. | 606/108 |
| 6,629,951 B2 * | 10/2003 | Laufer et al. | 604/96.01 |
| 6,632,243 B1 | 10/2003 | Zadno-Azizi et al. | 623/1.24 |
| 6,679,264 B1 | 1/2004 | Deem et al. | 128/207.16 |
| 6,694,979 B2 | 2/2004 | Deem et al. | 128/207.14 |
| 6,699,231 B1 | 3/2004 | Sterman et al. | 604/509 |
| 6,840,243 B2 | 1/2005 | Deem et al. | 128/207.16 |
| 6,878,141 B1 | 4/2005 | Perkins et al. | |
| 7,100,616 B2 | 9/2006 | Springmeyer | |
| 2001/0025132 A1 | 9/2001 | Alferness et al. | 600/37 |
| 2001/0037808 A1 * | 11/2001 | Deem et al. | 128/200.24 |
| 2001/0041906 A1 | 11/2001 | Gonzalez | 606/191 |
| 2001/0051799 A1 | 12/2001 | Ingenito | 604/516 |
| 2001/0052344 A1 | 12/2001 | Doshi | 128/207 |
| 2001/0056274 A1 | 12/2001 | Perkins et al. | 604/516 |
| 2002/0007831 A1 | 1/2002 | Davenport et al. | 128/200.24 |
| 2002/0026233 A1 | 2/2002 | Shaknovich | 623/1.24 |
| 2002/0062120 A1 | 5/2002 | Perkins et al. | 604/516 |
| 2002/0077593 A1 | 6/2002 | Perkins et al. | 604/96.01 |
| 2002/0077696 A1 | 6/2002 | Zadno-Azizi et al. | 623/1.24 |
| 2002/0087153 A1 | 7/2002 | Roschak et al. | 606/27 |
| 2002/0095209 A1 | 7/2002 | Zadno-Azizi et al. | 623/1.24 |
| 2002/0111619 A1 | 8/2002 | Keast et al. | 606/41 |
| 2002/0111620 A1 | 8/2002 | Cooper et al. | 606/41 |
| 2002/0112729 A1 | 8/2002 | DeVore et al. | 128/207.15 |
| 2002/0138135 A1 | 9/2002 | Duerig et al. | 623/1.24 |
| 2003/0018327 A1 | 1/2003 | Truckai et al. | 606/32 |
| 2003/0018344 A1 | 1/2003 | Kaji et al. | 606/130 |
| 2003/0050648 A1 | 3/2003 | Alferness et al. | 606/108 |
| 2003/0070682 A1 | 4/2003 | Wilson et al. | 128/207.16 |
| 2003/0070683 A1 | 4/2003 | Deem et al. | 128/207.16 |
| 2003/0075169 A1 | 4/2003 | Deem et al. | 128/200.19 |
| 2003/0075170 A1 | 4/2003 | Deem et al. | 128/200.19 |
| 2003/0083671 A1 | 5/2003 | Rimbaugh et al. | 606/108 |
| 2003/0127090 A1 | 7/2003 | Gifford et al. | 128/200.24 |
| 2003/0164168 A1 | 9/2003 | Shaw et al. | 128/200.24 |
| 2003/0192550 A1 | 10/2003 | Deem et al. | 128/207.14 |
| 2003/0192551 A1 | 10/2003 | Deem et al. | 128/207.14 |
| 2003/0199972 A1 | 10/2003 | Zadno-Azizi et al. | 623/1.24 |
| 2003/0212452 A1 | 11/2003 | Zadno-Azizi et al. | 623/1.24 |
| 2003/0228344 A1 | 12/2003 | Fields et al. | 424/423 |
| 2004/0016435 A1 | 1/2004 | Deem et al. | 128/207.14 |
| 2004/0039250 A1 | 2/2004 | Tholfsen et al. | 600/104 |
| 2004/0055606 A1 | 3/2004 | Hendricksen et al. | 128/207.14 |
| 2004/0060563 A1 * | 4/2004 | Rapacki et al. | 128/207.14 |
| 2004/0074491 A1 | 4/2004 | Hendricksen et al. | 128/200.19 |
| 2004/0089306 A1 | 5/2004 | Hundertmark et al. | 128/207.14 |
| 2004/0134487 A1 | 7/2004 | Deem et al. | 128/200.19 |
| 2004/0148035 A1 | 7/2004 | Barrett et al. | 623/23.65 |
| 2004/0154621 A1 | 8/2004 | Deem et al. | 128/206.24 |
| 2005/0016530 A1 | 1/2005 | McCutcheon et al. | 128/200.24 |
| 2005/0051163 A1 | 3/2005 | Deem et al. | 128/200.24 |
| 2005/0066974 A1 | 3/2005 | Fields et al. | 128/207.14 |
| 2006/0200076 A1 | 9/2006 | Gonzalez et al. | |
| 2006/0264772 A1 | 11/2006 | Aljuri et al. | |

FOREIGN PATENT DOCUMENTS

| | | |
|---|---|---|
| EP | 1 078 601 | 2/2001 |
| EP | 01/28433 | 4/2001 |
| EP | 1 151 729 | 11/2001 |
| GB | 2324729 | 4/1998 |
| RU | 2140211 | 10/1999 |
| SU | 852321 | 7/1981 |
| SU | 1371700 | 2/1988 |
| SU | 1593651 | 9/1990 |
| WO | 94/26175 | 11/1994 |
| WO | 95/32018 | 11/1995 |
| WO | 96/34582 | 11/1996 |
| WO | 97/44085 | 11/1997 |
| WO | 98/00840 | 1/1998 |
| WO | 98/19633 | 5/1998 |
| WO | 98/39047 | 9/1998 |
| WO | 98/44854 | 10/1998 |
| WO | 98/48706 | 11/1998 |
| WO | 99/01076 | 1/1999 |
| WO | 99/13801 | 3/1999 |
| WO | 99/26692 | 6/1999 |
| WO | 99/32040 | 7/1999 |
| WO | 99/42059 | 8/1999 |
| WO | 99/42161 | 8/1999 |
| WO | 99/64109 | 12/1999 |
| WO | 00/15149 | 3/2000 |

| | | |
|---|---|---|
| WO | 00/42950 | 7/2000 |
| WO | 00/51510 | 9/2000 |
| WO | 00/62699 | 10/2000 |
| WO | 00/78386 | 12/2000 |
| WO | 00/78407 | 12/2000 |
| WO | 01/02042 | 1/2001 |
| WO | 01/03642 | 1/2001 |
| WO | 01/05334 | 1/2001 |
| WO | 01/10313 | 2/2001 |
| WO | 01/10314 | 2/2001 |
| WO | 01/12104 | 2/2001 |
| WO | 01/13839 | 3/2001 |
| WO | 01/13908 | 3/2001 |
| WO | 01/45590 | 6/2001 |
| WO | 01/49213 | 7/2001 |
| WO | 01/54585 | 8/2001 |
| WO | 01/54625 | 8/2001 |
| WO | 01/54685 | 8/2001 |
| WO | 01/66190 | 9/2001 |
| WO | 01/74271 | 10/2001 |
| WO | 01/87170 | 11/2001 |
| WO | 01/89366 | 11/2001 |
| WO | 01/95786 | 12/2001 |
| WO | 02/05884 | 1/2002 |
| WO | 02/22072 | 3/2002 |
| WO | 02/32333 | 4/2002 |
| WO | 02/34322 | 5/2002 |
| WO | 02/38038 | 5/2002 |
| WO | 02/47575 | 6/2002 |
| WO | 02/056794 | 7/2002 |
| WO | 02/064045 | 8/2002 |
| WO | 02/064190 | 8/2002 |
| WO | 02/069823 | 9/2002 |
| WO | 02/094087 | 11/2002 |
| WO | 03/022124 | 3/2003 |
| WO | 03/030975 | 4/2003 |
| WO | 03/041779 | 5/2003 |
| WO | 03/075796 | 9/2003 |
| WO | 03/099164 | 12/2003 |
| WO | 2004/010845 | 2/2004 |
| WO | 2004/049974 | 6/2004 |
| WO | 2005/007023 | 1/2005 |

OTHER PUBLICATIONS

Derwent# 007607249 WPI Acc. No. 1988-241181/198834 (citing Russian Application No. SU4026409, published Feb. 21, 1986), Russian Patent No. SU 1371700.

Derwent# 008650867 WPI Acc. No. 1991-154896/199121 (citing Russian Application No. SU4280143, published Jul. 7, 1987), Russian Patent No. SU 1593651.

Harris et al., "The Experimental Production in Dogs of Emphysema with Associated Asthmatic Syndrome by Means of an Intratracheal Ball Valve", *J. Lab. Clini. Med.*, 9(iv):75-88, 1919.

Lewis et al., "Pulmonary Interstitial Emphysema: Selective Broncial Occlusion with a Swan-Ganz Catheter", *Archives of Disease in Childhood*, 63:313-315, 1988.

Mathew et al., "Selective bronchial obstruction for treatment of bullous interstitial emphysema." *J. of Ped.*, 96:475-477, 1980.

Okada et al., "Emergent Bronchofiberoptic Bronchial Occlusion for Intractable Pneumothorax with Severe Emphysema", *The Jap. J. of Thor. And Cardio. Sur.*, 46:1078-1081, 1998.

Puhakka et al., "Acute Bronchial Obstruction: An Experimental Rabbit Model Study", *Int. J. of Pediatric Otorhinolaryngology*, 18:107-118, 1989.

Snider et al., *The Definition of Emphysema*: Report of the National Heart Lung and Blood Institute, Division of Lung Diseases Workshop, *Am. Rev. Respir. Dis.*, 132:182-185, 1985.

Woodring et al., "Pneumothorax ex Vacuo", *CHEST*, 100:1102-1124, 1996.

\* cited by examiner

FIG. 7

METHODS AND DEVICES FOR BLOCKING FLOW THROUGH COLLATERAL PATHWAYS IN THE LUNG

REFERENCE TO PRIORITY DOCUMENT

This application claims priority of U.S. Provisional Patent Application Ser. No. 60/548,791 entitled "Methods and Devices for Blocking Flow Through Collateral Pathways in the Lung", filed Feb. 27, 2004. Priority of the filing date of Feb. 27, 2005 is hereby claimed, and the disclosure of the Provisional Patent Application is hereby incorporated by reference.

BACKGROUND

Various devices can be used to achieve the bronchial isolation of one or more selected regions of the lung. Pursuant to a lung region bronchial isolation process, at least one flow control device (also referred to as a bronchial isolation device) is implanted within one or more bronchial passageways that provide fluid flow to and from the lung region to thereby "isolate" the lung region. The lung region is isolated in that fluid flow to and from the lung region is regulated or blocked through the bronchial passageway(s) in which the device is implanted.

For example, the flow of fluid (gas or liquid) past the device in the inhalation direction can be prevented while allowing flow of fluid in the exhalation direction, or the flow of fluid past the implanted device in both the inhalation and exhalation directions can be prevented. The flow control devices can comprise, for example, one-way valves, two-way valves, occluders or blockers, ligating clips, glues, sealants, sclerosing agents, etc.

It should be appreciated that even with the implanted isolation devices properly deployed, air can in certain circumstances flow into the isolated lung region via a collateral pathway. This can result in the diseased region of the lung still receiving air even though the isolation devices were implanted into the direct pathways to the lung. Collateral flow can be, for example, air flow that flows between segments of a lung, or it can be, for example, air flow that flows between lobes of a lung, as described in more detail below.

Collateral flow into an isolated lung region can make it difficult to achieve a desired flow dynamic for the lung region. Moreover, it has been shown that as the disease progresses, the collateral flow throughout the lung can increase, which makes it even more difficult to properly isolate a diseased lung region by simply implanting flow control valves in the bronchial passageways that directly feed air to the diseased lung region.

Given that the lung can have collateral gas flow pathways in the lung that could keep the isolated portion of the lung inflated, it is desirable to occlude these collateral flow channels in order to allow the lung to collapse through absorption of the trapped gas, or by exhalation of the trapped gas out through implanted one-way or two-way valve bronchial isolation devices.

SUMMARY

Disclosed is a method of regulating fluid flow for a targeted lung region. The method comprises injecting a therapeutic agent into the targeted lung region. The therapeutic agent induces a reaction in lung tissue of the targeted lung region or in a collateral pathway to the lung region to reduce collateral fluid flow into the targeted lung region. In one aspect, the method additionally comprises deploying a bronchial isolation device in the direct pathway to regulate fluid flow to the targeted lung region through the direct pathway. The therapeutic agent can comprise, for example, a sclerosing agent that induces a reaction that causes sclerosis in the lung tissue.

Also disclosed is a method of regulating fluid flow for a targeted lung region. The method comprises reducing collateral fluid flow that flows through a collateral pathway to the targeted lung region. After reducing collateral flow to the targeted lung region, and direct fluid flow in a direct pathway is redirected. The direct pathway provides direct fluid flow to the targeted lung region.

Throughout this disclosure, reference is sometimes made to a "direct pathway" to a targeted lung region and to a "collateral pathway" to a targeted lung region. The term "direct pathway" refers to a bronchial passageway that branches directly or indirectly from the trachea and either (1) terminates in the targeted lung region to thereby directly provide air to the targeted lung region; or (2) branches into at least one other bronchial passageway that terminates in the targeted lung region to thereby directly provide air to the targeted lung region. The term "collateral pathway" refers to any pathway that provides air to the targeted lung region and that is not a direct pathway.

The term "direct" is used to refer to air flow that flows into or out of a targeted lung region via a direct pathway. Likewise, the term "collateral" is used to refer to fluid flow (such as air flow) that flows into or out of a targeted lung region via a collateral pathway.

The details of one or more embodiments are set forth in the accompanying drawings and the description below. Other features, objects, and advantages will be apparent from the description and drawings, and from the claims.

DETAILED DESCRIPTION

Disclosed herein are methods and devices for sealing collateral flow pathways into a target lung region and/or reducing or eliminating collateral flow into the target lung region, such as, for example, to achieve a desired fluid flow dynamic to a lung region during respiration and/or to induce collapse in one or more lung regions that are supplied air through one or more collateral pathways.

As described in more detail below, an identified region of the lung (referred to herein as the "targeted lung region") is targeted for flow regulation. Collateral flow to the targeted lung region is then reduced or prevented pursuant to various methods and devices described herein. Various procedures for blocking collateral flow to the targeted lung region are described below.

Figure 1:
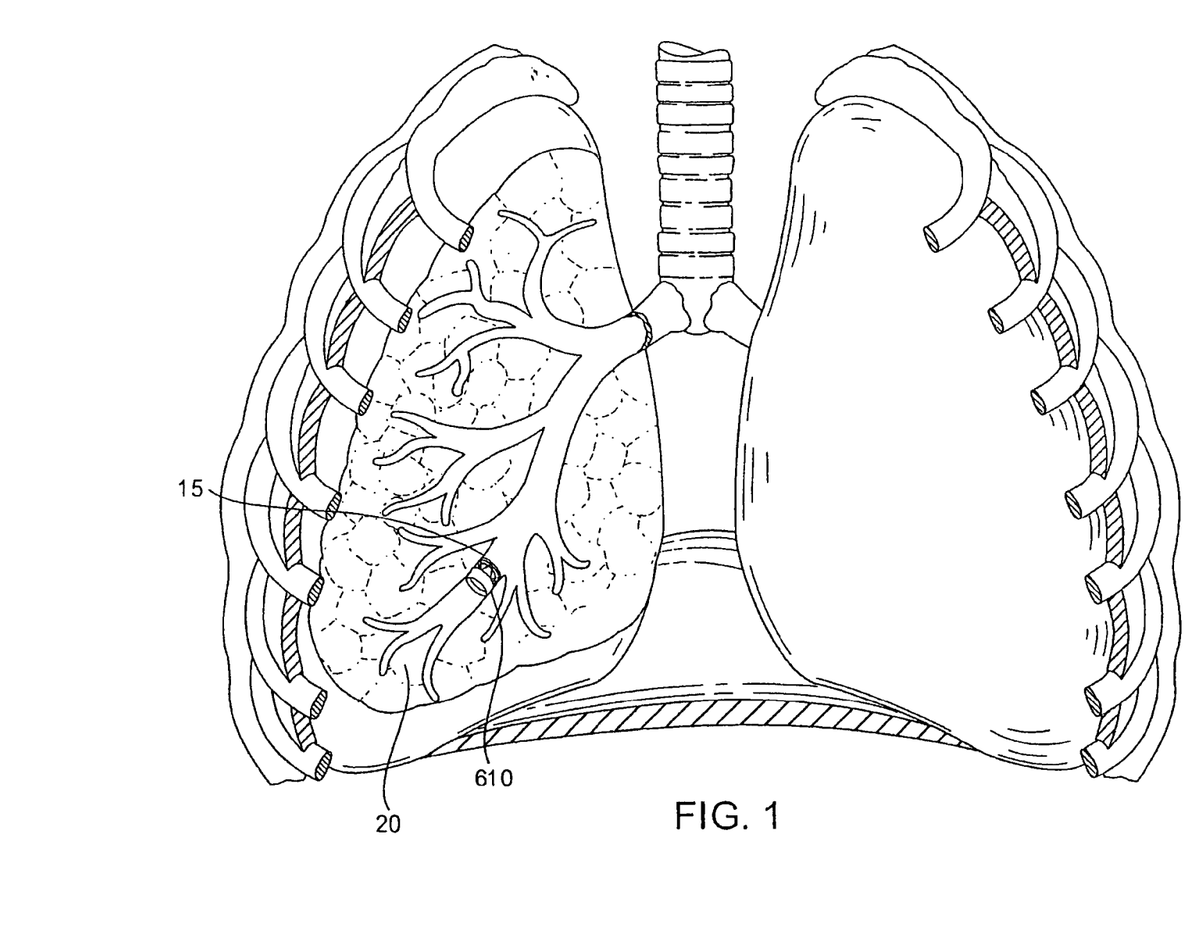
FIG. 1 shows an anterior view of a pair of human lungs and a bronchial tree with a bronchial isolation device implanted in a bronchial passageway.

Direct flow to the targeted lung region can optionally be reduced or prevented, such as by positioning a bronchial isolation device in a direct pathway to the targeted lung region to inhibit or completely block fluid flow through the direct pathway. As shown in FIG. 1, in one exemplary embodiment, a bronchial isolation device 610 is optionally implanted into the lung. The device 610 is implanted into a bronchial passageway 15 that feeds air to a targeted lung region 20. The bronchial isolation device 610 regulates airflow through the bronchial passageway 15, such as by permitting fluid flow in one direction (e.g., the exhalation direction) while limiting or preventing fluid flow in another direction (e.g., the inhalation direction).

Figure 2A:
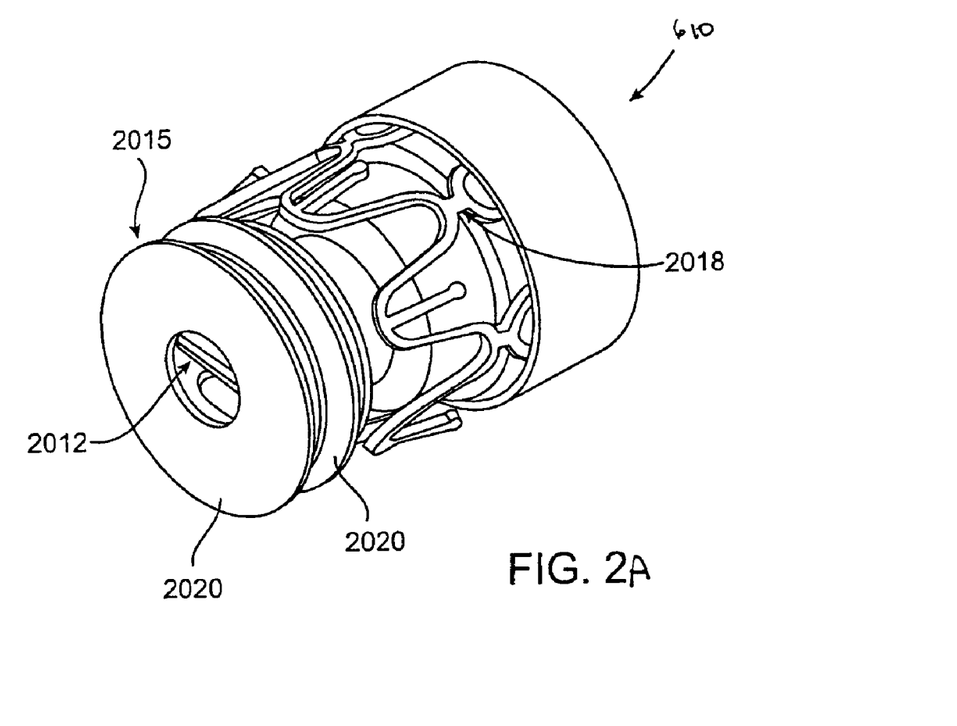
FIG. 2A shows a perspective view of an embodiment of a bronchial isolation device.
Figure 2B:
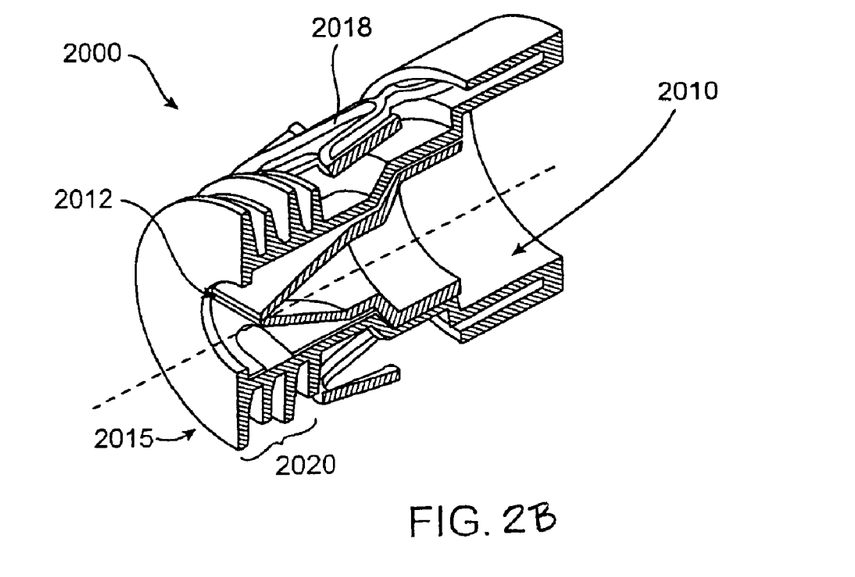
FIG. 2B shows a cross-sectional view of the device of FIG. 2A.

FIGS. 2A and 2B show an exemplary bronchial isolation device 610 that can be used to achieve one-way flow. The flow control element 610 includes a main body that defines an interior lumen 2010 through which fluid can flow along a flow path. The flow of fluid through the interior lumen 2010 is controlled by a valve member 2012. The valve member 2012 in FIGS. 2A, 2B is a one-way valve, although two-way valves can also be used, depending on the type of flow regulation desired.

With reference still to FIGS. 2A and 2B, the bronchial isolation device 610 has a general outer shape and contour that permits the flow control bronchial isolation device to fit entirely within a body passageway, such as within a bronchial passageway. The bronchial isolation device 610 includes an outer seal member 2015 that provides a seal with the internal walls of a body passageway when the bronchial isolation device is implanted into the body passageway. The seal member 2015 includes a series of radially-extending, circular flanges 2020 that surround the outer circumference of the bronchial isolation device 610. The bronchial isolation device 610 also includes an anchor member 2018 that functions to anchor the bronchial isolation device 610 within a body passageway.

The following references describe exemplary bronchial isolation devices and delivery devices: U.S. Pat. No. 5,954, 766 entitled "Body Fluid Flow Control Device"; U.S. patent application Ser. No. 09/797,910, entitled "Methods and Devices for Use in Performing Pulmonary Procedures"; U.S. patent application Ser. No. 10/270,792, entitled "Bronchial Flow Control Devices and Methods of Use"; U.S. patent application Ser. No. 10/448,154, entitled "Guidewire Delivery of Implantable Bronchial Isolation Devices in Accordance with Lung Treatment"; and U.S. patent application Ser. No. 10/275,995, entitled "Bronchiopulmonary Occlusion Devices and Lung Volume Reduction Methods". The foregoing references are all incorporated by reference in their entirety and are all assigned to Emphasys Medical, Inc., the assignee of the instant application. It should be appreciated that other types of bronchial isolation devices can be used.

U.S. Provisional Patent Application Ser. No. 60/363,328, entitled "Methods and Devices for Inducing Collapse in Lung Regions Fed by Collateral Pathways" and U.S. patent application Ser. No. 10/384,899 entitled "Methods and Devices for Inducing Collapse in Lung Regions Fed by Collateral Pathways", which are both incorporated herein by reference, described various methods and devices for blocking collateral flow into portions of the lung targeted for collapse. Improvements on these methods and devices are described herein.

Exemplary Lung Regions

Throughout this disclosure, reference is made to the term "lung region". As used herein, the term "lung region" refers to a defined division or portion of a lung. For purposes of example, lung regions are described herein with reference to human lungs, wherein some exemplary lung regions include lung lobes and lung segments. Thus, the term "lung region" as used herein can refer, for example, to a lung lobe or a lung segment. Such nomenclature conform to nomenclature for portions of the lungs that are known to those skilled in the art. However, it should be appreciated that the term "lung region" does not necessarily refer to a lung lobe or a lung segment, but can refer to some other defined division or portion of a human or non-human lung.

Figure 3:
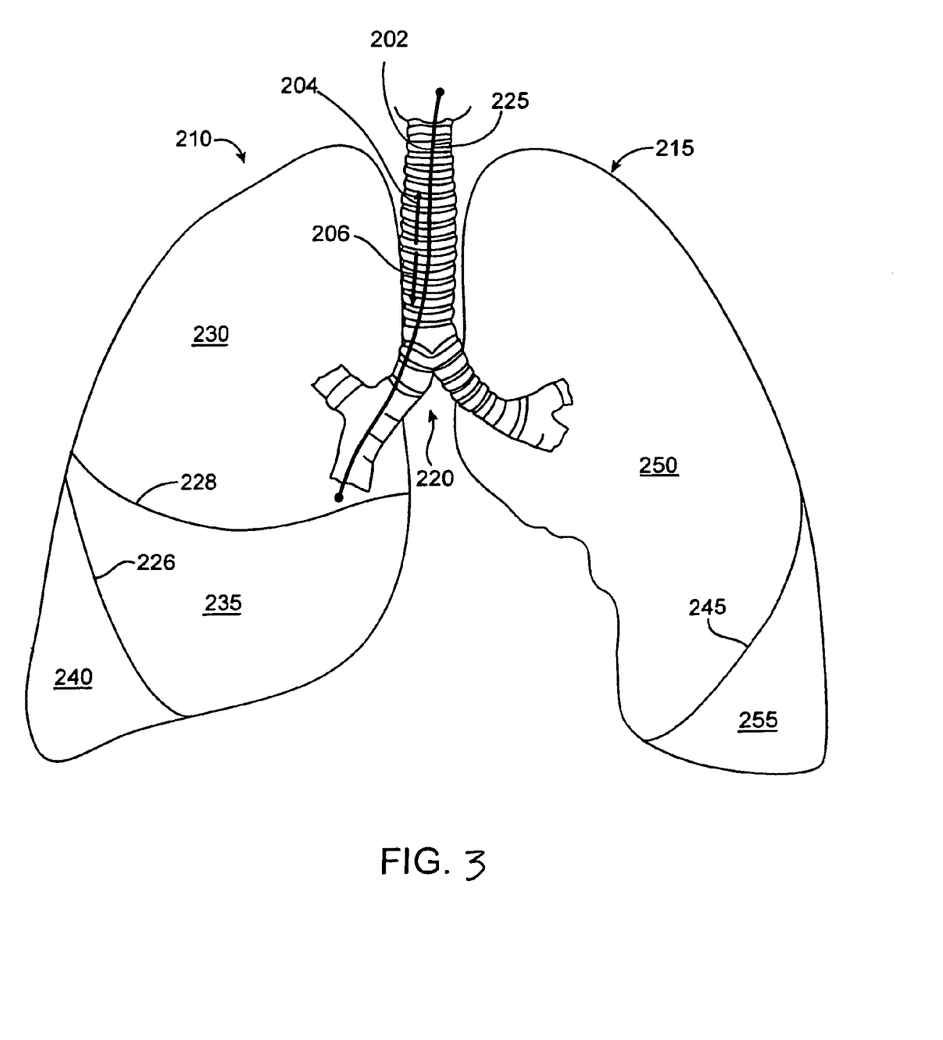
FIG. 3 illustrates an anterior view of a pair of human lungs and a bronchial tree.

FIG. 3 shows an anterior view of a pair of human lungs 210, 215 and a bronchial tree 220 that provides a fluid pathway into and out of the lungs 210, 215 from a trachea 225, as will be known to those skilled in the art. As used herein, the term "fluid" can refer to a gas, a liquid, or a combination of gas(es) and liquid(s). For clarity of illustration, FIG. 3 shows only a portion of the bronchial tree 220, which is described in more detail below with reference to FIG. 6.

Throughout this description, certain terms are used that refer to relative directions or locations along a path defined from an entryway into the patient's body (e.g., the mouth or nose) to the patient's lungs. The path of airflow into the lungs generally begins at the patient's mouth or nose, travels through the trachea into one or more bronchial passageways, and terminates at some point in the patient's lungs.

For example, FIG. 3 shows a path 202 that travels through the trachea 225 and through a bronchial passageway into a location in the right lung 210. The term "proximal direction" refers to the direction along such a path 202 that points toward the patient's mouth or nose and away from the patient's lungs. In other words, the proximal direction is generally the same as the expiration direction when the patient breathes. The arrow 204 in FIG. 3 points in the proximal or expiratory direction. The term "distal direction" refers to the direction along such a path 202 that points toward the patient's lung and away from the mouth or nose. The distal direction is generally the same as the inhalation or inspiratory direction when the patient breathes. The arrow 206 in FIG. 3 points in the distal or inhalation direction.

The lungs include a right lung 210 and a left lung 215. The right lung 210 includes lung regions comprised of three lobes, including a right upper lobe 230, a right middle lobe 235, and a right lower lobe 240. The lobes 230, 235, 240 are separated by two interlobar fissures, including a right oblique fissure 226 and a right transverse fissure 228. The right oblique fissure 226 separates the right lower lobe 240 from the right upper lobe 230 and from the right middle lobe 235. The right transverse fissure 228 separates the right upper lobe 230 from the right middle lobe 235.

As shown in FIG. 3, the left lung 215 includes lung regions comprised of two lobes, including the left upper lobe 250 and the left lower lobe 255. An interlobar fissure comprised of a left oblique fissure 245 of the left lung 215 separates the left upper lobe 250 from the left lower lobe 255. The lobes 230, 235, 240, 250, 255 are directly supplied, air via respective lobar bronchi, as described in detail below.

Figure 4:
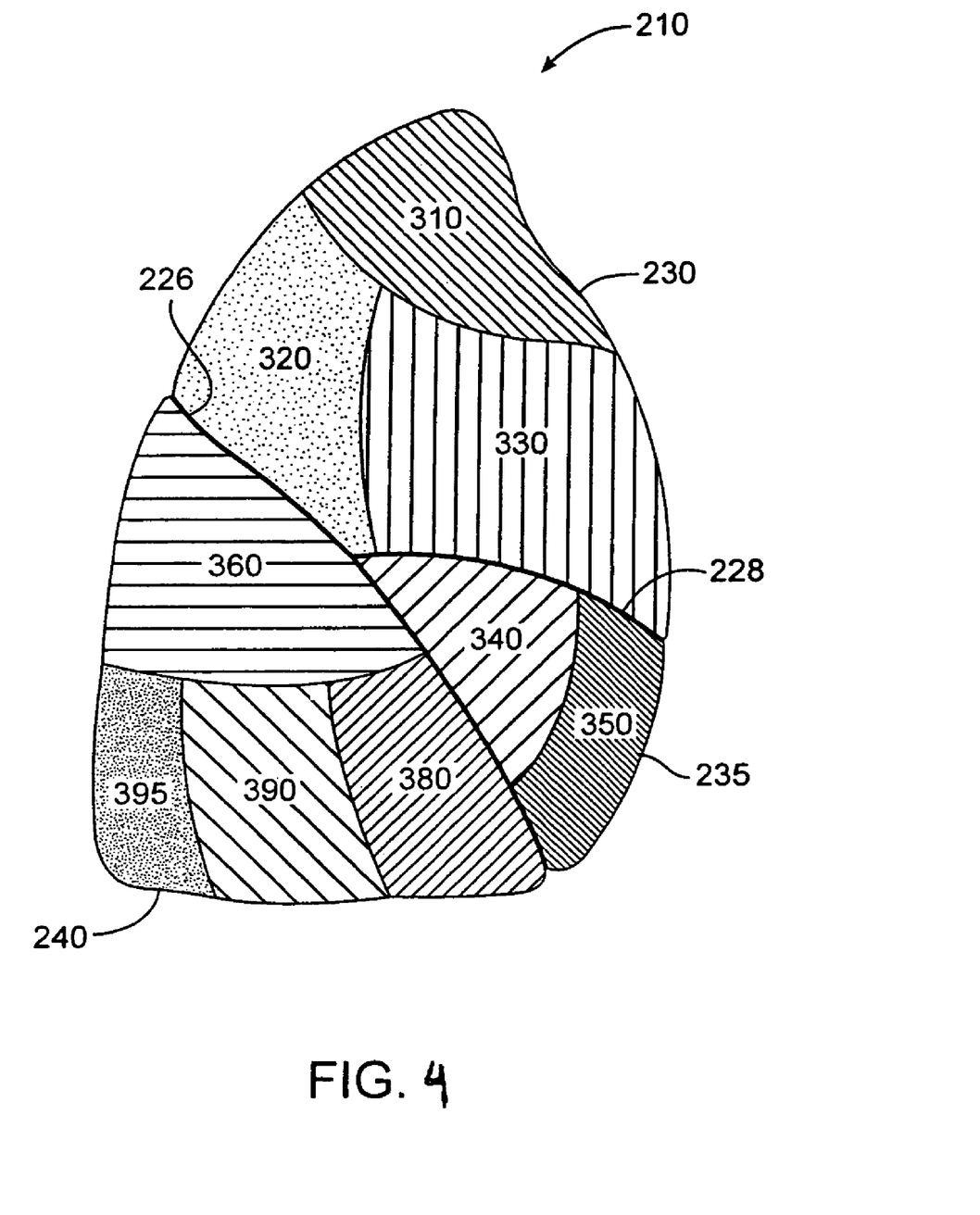
FIG. 4 illustrates a lateral view of the right lung.

FIG. 4 is a lateral view of the right lung 210. The right lung 210 is subdivided into lung regions comprised of a plurality of bronchopulmonary segments. Each bronchopulmonary segment is directly supplied air by a corresponding segmental tertiary bronchus, as described below. The bronchopulmonary segments of the right lung 210 include a right apical segment 310, a right posterior segment 320, and a right anterior segment 330, all of which are disposed in the right upper lobe 230. The right lung bronchopulmonary segments further include a right lateral segment 340 and a right medial segment 350, which are disposed in the right middle lobe 235. The right lower lobe 240 includes bronchopulmonary segments comprised of a right superior segment 360, a right medial basal segment (which cannot be seen from the lateral view and is not shown in FIG. 4), a right anterior basal segment 380, a right lateral basal segment 390, and a right posterior basal segment 395.

Figure 5:
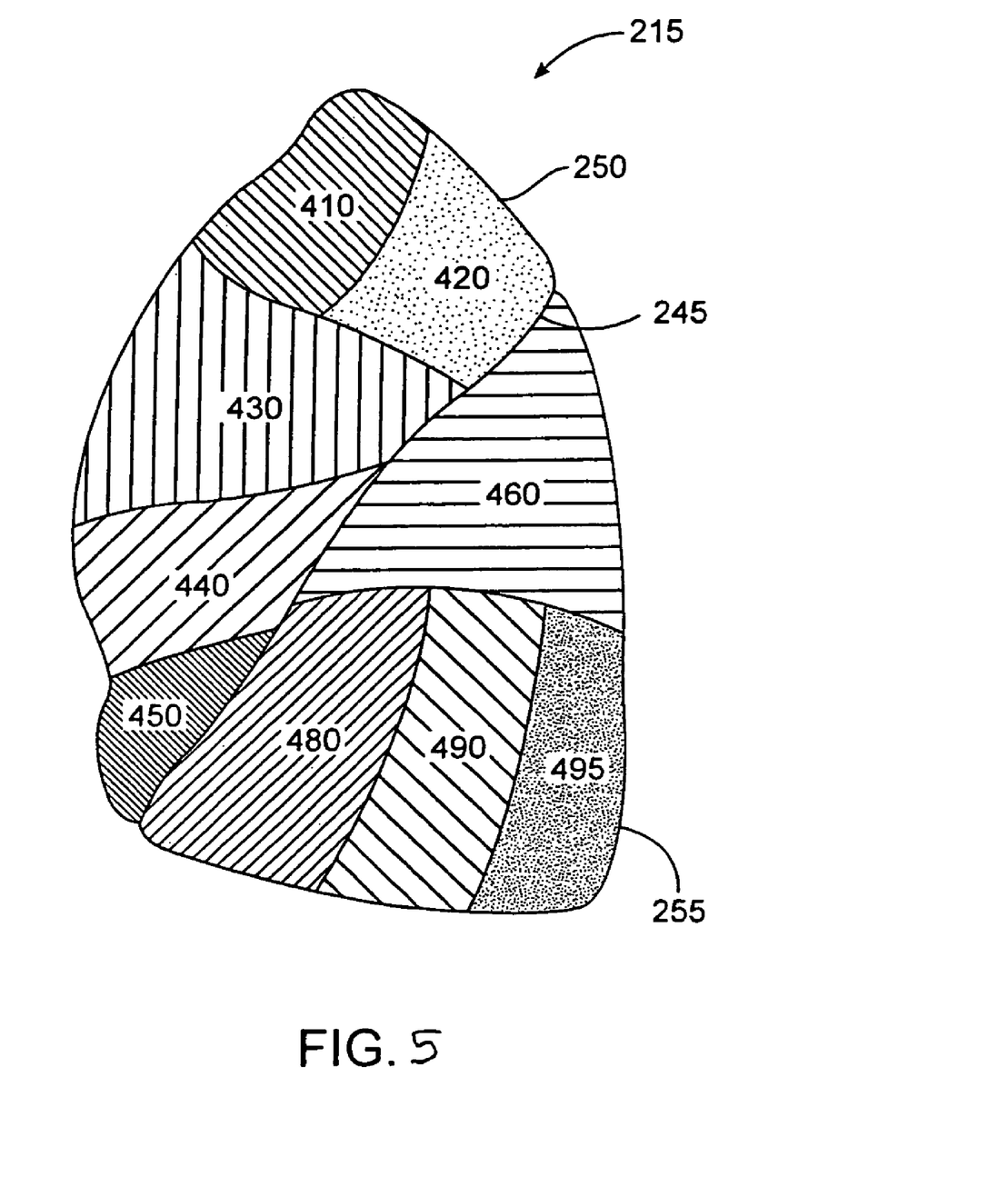
FIG. 5 illustrates a lateral view of the left lung.

FIG. 5 shows a lateral view of the left lung 215, which is subdivided into lung regions comprised of a plurality of bronchopulmonary segments. The bronchopulmonary segments include a left apical segment 410, a left posterior segment 420, a left anterior segment 430, a left superior segment 440, and a left inferior segment 450, which are disposed in the left lung upper lobe 250. The lower lobe 255 of the left lung 215 includes bronchopulmonary segments comprised of a left superior segment 460, a left medial basal segment (which cannot be seen from the lateral view and is not shown in FIG. 5), a left anterior basal segment 480, a left lateral basal segment 490, and a left posterior basal segment 495.

Figure 6:
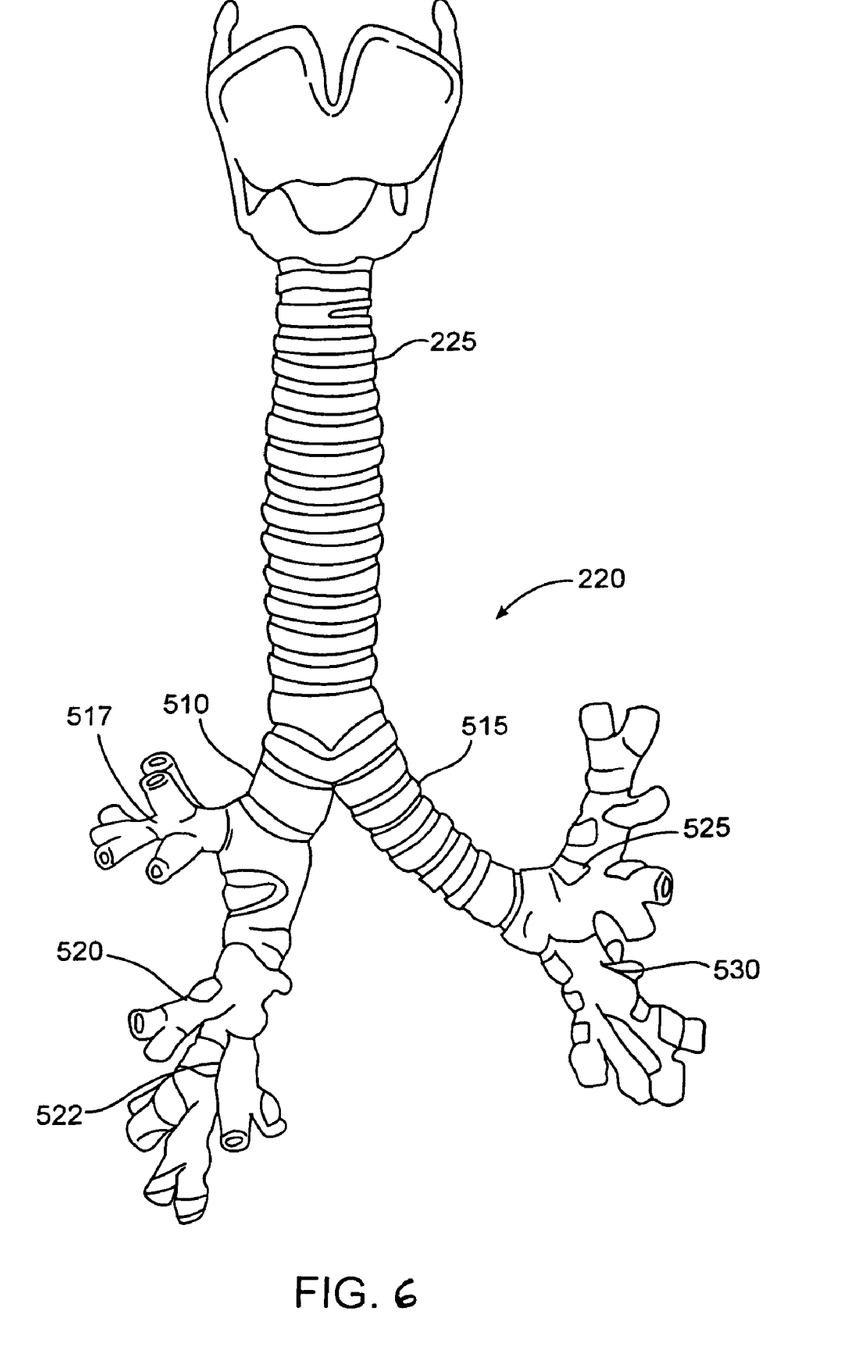
FIG. 6 illustrates an anterior view of the trachea and a portion of the bronchial tree.

FIG. 6 shows an anterior view of the trachea 225 and a portion of the bronchial tree 220, which includes a network of bronchial passageways, as described below. The trachea 225 divides at a lower end into two bronchial passageways comprised of primary bronchi, including a right primary bronchus 510 that provides direct air flow to the right lung 210, and a left primary bronchus 515 that provides direct air flow to the left lung 215. Each primary bronchus 510, 515 divides into a next generation of bronchial passageways comprised of a plurality of lobar bronchi. The right primary bronchus 510 divides into a right upper lobar bronchus 517, a right middle lobar bronchus 520, and a right lower lobar bronchus 422. The left primary bronchus 515 divides into a left upper lobar bronchus 525 and a left lower lobar bronchus 530.

Each lobar bronchus 517, 520, 522, 525, 530 directly feeds fluid to a respective lung lobe, as indicated by the respective names of the lobar bronchi. The lobar bronchi each divide into yet another generation of bronchial passageways comprised of segmental bronchi, which provide air flow to the bronchopulmonary segments discussed above.

As is known to those skilled in the art, a bronchial passageway defines an internal lumen through which fluid can flow to and from a lung or lung region. The diameter of the internal lumen for a specific bronchial passageway can vary based on the bronchial passageway's location in the bronchial tree (such as whether the bronchial passageway is a lobar bronchus or a segmental bronchus) and can also vary from patient to patient. However, the internal diameter of a bronchial passageway is generally in the range of 3 millimeters (mm) to 10 mm, although the internal diameter of a bronchial passageway can be outside of this range. For example, a bronchial passageway can have an internal diameter of well below 1 mm at locations deep within the lung. The internal diameter can also vary from inhalation to exhalation as the diameter increases during inhalation as the lungs expand, and decreases during exhalation as the lungs contract.

Blocking of Collateral Flow

When a portion of the lung is targeted for isolation, such as, for example, to collapse the targeted lung region or to modify the fluid (gas or liquid) flow into and out of the targeted lung region, the presence of collateral pathways can allow unregulated gas to flow into and out of the targeted region. These collateral pathways can exists between portions of the lung within the same lobe, or can exist between lobes. As mentioned above, in these situations it is desirable to stop flow through these collateral pathways in order to allow isolation of the targeted lung tissue.

Throughout this disclosure, reference is sometimes made to a "direct pathway" to a targeted lung region and to a "collateral pathway" to a targeted lung region. The term "direct pathway" refers to a bronchial passageway that branches directly or indirectly from the trachea and either (1) terminates in the targeted lung region to thereby directly provide air to the targeted lung region; or (2) branches into at least one other bronchial passageway that terminates in the targeted lung region to thereby directly provide air to the targeted lung region. The term "collateral pathway" refers to any pathway that provides air to the targeted lung region and that is not a direct pathway.

The term "direct" is used to refer to air flow that flows into or out of a targeted lung region via a direct pathway. Likewise, the term "collateral" is used to refer to fluid flow (such as air flow) that flows into or out of a targeted lung region via a collateral pathway. Thus, for example, "direct" flow is fluid flow (such as air flow) that enters or exits the targeted lung region via a direct pathway, and "collateral" flow is fluid flow (such as air flow) that enters or exits the targeted lung region via a collateral pathway. A collateral flow can be, for example, air flow that flows between segments of a lung, which is referred to as intralobar flow, or it can be, for example, air flow that flows between lobes of a lung, which is referred to as interlobar flow.

There are several procedures or components that can be used to block or otherwise alter collateral flow and/or direct flow pursuant to the methods described herein:

1. Bronchial isolation device(s);
2. A bulking agent or carrier;
3. A local anesthetic;
4. An inflammatory or sclerosing agent;
5. Suction.

Any of the aforementioned components or procedures can be used alone or in various combinations in order to inhibit or completely stop flow through collateral pathways and to inhibit or completely stop flow through direct pathways. The components are now described.

1. Bronchial Isolation Devices

As discussed, bronchial isolation devices can be one-way valves that allow flow in the exhalation direction only, occluders or plugs that prevent flow in either direction, or two-way valves that control flow in both directions.

As discussed with reference to FIGS. 1, 2A, and 2B, the bronchial isolation device 610 can be implanted in a bronchial passageway to regulate the flow of fluid through the bronchial passageway. When implanted in a bronchial passageway, the bronchial isolation device 610 anchors within the bronchial passageway in a sealing fashion such that fluid in the bronchial passageway must pass through the flow control device in order to travel past the location where the flow control device is located.

The bronchial isolation device 610 has fluid flow regulation characteristics that can be varied based upon the design of the flow control device. For example, the bronchial isolation device 610 can be configured to either permit fluid flow in two directions (i.e., proximal and distal directions), permit fluid flow in only one direction (proximal or distal direction), completely restrict fluid flow in any direction through the flow control device, or any combination of the above. The bronchial isolation device can be configured such that when fluid flow is permitted, it is only permitted above a certain pressure, referred to as the cracking pressure. The bronchial isolation device 610 can also be configured such that a device, such as a catheter, can be manually inserted through the bronchial isolation device 610 to allow, for example, access to the distal side of the device after implantation.

2. Bulking Agents and Carriers

A therapeutic agent comprised of a bulking agent can be used to fill space (such as space within the targeted lung region and/or a collateral pathway to the targeted lung region) and thereby partially or entirely seal off collateral flow into the targeted lung region.

Various substances can be used as bulking agents and carriers. Some exemplary substances that can be used as bulking agents and carriers include hydrogel and autologous blood among others. A hydrogel is defined as a colloidal gel in which water is the dispersion medium, and a colloid is defined as a mixture with properties between those of a solution and fine suspension. Hydrogels can be used as implantable bulking agents as well as a carrier for other therapeutic agents as the hydrogel can be designed to be absorbed slowly by the body, thus releasing the therapeutic agent into surrounding tissue over time.

One particularly useful form of hydrogel is the Pluronic family of products produced by BASF Corp, which is located in Mt. Olive, N.J. 07828, USA. One such substance, Pluronic F-127, is a hydrogel that is a polymer of polyoxyethylene (PEO) and polyoxypropylene (PPO) with two 96-unit hydrophilic PEO chains surrounding one 69-unit hydrophobic PPO chain. The result is a non-ionic surfactant that, when placed in an aqueous solution, at or above room temperature converts from a liquid state to that of a non-fluid hydrogel. If it is implanted in the body, it can act as a temporary bulking agent that will be absorbed over time, or it can be combined with other therapeutic agents, and these agents will be released slowing into the body as the hydrogel is absorbed.

Hydrogel can be modified so that it becomes thermo-responsive in that it will have different viscosities at different temperature. SMART Hydrogel™, produced by Advanced Medical Solutions Ltd. (Road Three, Winsford Industrial Estate, Winsford, Cheshire CW7 3PD, United Kingdom), is a hydrogel that is a combination of Pluronic F-127 and polyacrylic acid. The result is a hydrogel that has a viscosity close to water at room temperature, and a thick gel-like viscosity at 37 deg C. (body temperature). This allows the hydrogel to be injected easily into a location in the body in its more liquid form, whereby it viscosities and forms a thick gel once it reaches the intended implant location and is raised to body temperature.

3. Local Anesthetic

A therapeutic agent comprised of a local anesthetic can be used to reduce or eliminate pain or irritation from the injection of foreign substances into the lung. Lidocaine is an exemplary local anesthetic. As described below, the local anesthetic can be combined with another component, such as the bulking agent or inflammatory or sclerosing agent to inhibit or completely stop flow through collateral pathways.

4. Inflammatory or Sclerosing Agent

A therapeutic agent comprised of an inflammatory or sclerosing agent can be used to temporarily or permanently close collateral pathways by causing the collateral pathways to swell closed. Inflammatory or sclerosing agents that can be effective in the lung include antibiotics such as tetracycline, doxycycline, minocycline, pneumococcus culture, etc.

5. Suction

The targeted lung region can be suctioned using a vacuum source through one or more suction catheters that are deployed at or near the targeted lung region. The suction catheter can be used to aspirate fluid from the targeted lung region by applying a suction to the proximal end of the catheter, and this suction is transferred to the distal region of the bronchial passageway through the internal lumen of the catheter.

The targeted lung region can be suctioned prior to injection of a therapeutic agent into the targeted lung region in order to remove fluid and either reduce the volume or collapse the targeted lung region. This reduction in volume or collapse of the targeted lung region serves to create space in the targeted lung region for injection of the therapeutic agent. As discussed below, suction can also be used after injection of the therapeutic agent, such as to suction the therapeutic agent from the targeted lung region. If a bronchial isolation device is implanted in the lung, the suction can be performed before the device is implanted or while the device is implanted, such as suctioning through the device. In this regard, the suction can be applied either distally or proximally of the implanted bronchial isolation device.

The suction can be applied either continuously or in a pulsatile manner, such as by using either a continuous or pulsatile vacuum source. In one embodiment, fluid can be aspirated from the targeted lung region using a very low vacuum source over a long period of time, such as one hour or more. In this case, the catheter may be inserted nasally and a water seal may control the vacuum source.

In one embodiment, pulsatile suction is defined as a vacuum source that varies in vacuum pressure from atmospheric pressure down to −10 cm H2O. The frequency of the pulse can be adjusted so that the collapsed bronchus has time to re-open at the trough of the suction wave prior to the next cycle. The frequency of the pulse can be fast enough such that the bronchus does not have time to collapse at the peak of the suction wave prior to the next cycle. The suction force can be regulated such that even at the peak suction, the negative pressure is not low enough to collapse the distal airways.

The frequency of the suction (either pulsatile or continuous) could be set to the patient's respiratory cycle such that negative pressure is applied only during inspiration. That is, the suction is synchronized with the patient's respiration such that continuous suction or a series of suction pulses are applied to the targeted lung region only while the patient is inhaling. This can allow the lung's tethering forces to be exerted thereby keeping the distal airways open.

One possible method of implementing pulsatile suction is to utilize a water manometer attached to a vacuum source. The vacuum regulator pipe in the water manometer can be manually or mechanically moved up and down at the desired frequency to the desired vacuum break point (0 to −10 cm). This is only an exemplary method of creating a pulsatile vacuum source and it should be appreciated that other methods can be used.

Bulking Agent Combined with Optional Bronchial Isolation Device

One way of blocking collateral flow into a targeted lung region is to inject a bulking agent (such as hydrogel) into the target lung region prior to isolating the targeted lung region with bronchial isolation devices. One method for implanting the bulking agent into the target region is to use a catheter.

Figure 7:
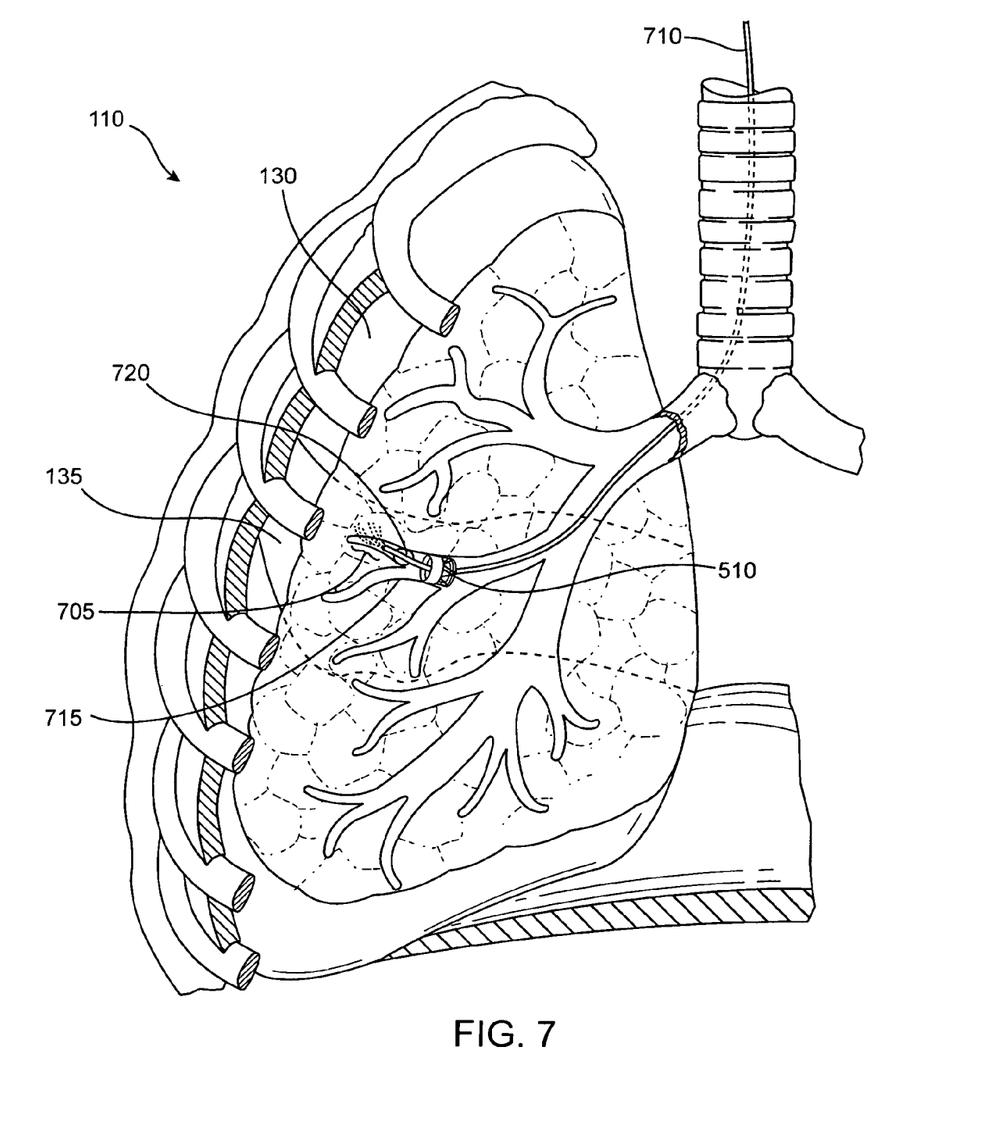
FIG. 7 shows an anterior view of a pair of human lungs and a bronchial tree with a catheter positioned in a bronchial passageway for injecting a therapeutic agent into a target region of the lung.

FIG. 7 illustrates an example of a method wherein a bulking agent 705 is delivered to a targeted lung region using a delivery catheter 710. The targeted lung region is located in the right middle lobe 135 of the right lung 110. The delivery catheter 710 can be a conventional delivery catheter of the type known to those of skill in the art. The delivery catheter 710 is deployed in a bronchial passageway, such as in the segmental bronchi 715, that leads to the targeted lung region. A bronchial isolation device 510 can optionally be deployed either before or after deployment of the delivery catheter 710 or need not be deployed at all. As mentioned, the targeted lung region can be suctioned prior to injection of the bulking agent.

Once the delivery catheter 710 is deployed in the targeted lung region, the bulking agent 705 can be delivered into the targeted lung region using the delivery catheter 710. This can be accomplished by passing the bulking agent through an internal lumen in the delivery catheter so that the agent exits a hole in the distal end of the delivery catheter 710 into the targeted lung region. As shown in FIG. 7, the distal end of the delivery catheter 710 can be sealed within the targeted lung region by inflating a balloon 720 that is disposed near the distal end of the catheter according to well-known methods. A balloon-tipped catheter is not necessary for use.

In order to track the dispersion of the bulking agent, or any other injected therapeutic agent, a small quantity of radiographic contrast can be mixed with the bulking agent prior to injecting the bulking agent. The extent and spread of the injection can then be monitored with fluoroscopy.

Prior to or after the bulking agent is injected, at least one bronchial isolation device can optionally implanted in the bronchial lumen(s) leading to the targeted lung region in order to restrict direct flow to the targeted tissue through the bronchial lumen, as described above. In this manner, the tissue is fully isolated. However, it should be appreciated that the bronchial isolation device is not required to be implanted in combination with use of the bulking agent. It should be appreciated that other methods of delivering the bulking agent to the target location are possible.

Sclerosing Agents Combined with Optional Bronchial Isolation Device

Rather than blocking flow with a bulking agent like hydrogel, a sclerosing agent can be injected into the targeted lung region to inflame and close off the collateral pathways. As with the bulking agent, one method for implanting the sclerosing agent into the target region is through the use of a catheter. A suitable catheter, such as a balloon catheter, is selected and inserted into a bronchial lumen leading to the target lung region. The sclerosing agent is then injected through the catheter until the targeted region is filled with sclerosing agent. If a balloon tipped catheter is used, the balloon is inflated in the target bronchial lumen prior to injection to prevent backflow of the sclerosing agent in the proximal direction during injection. As mentioned, the targeted lung region can be suctioned prior to injection of the sclerosing agent.

As discussed with respect to the bulking agent, a small quantity of radiographic contrast can be mixed with the agent in order to track the dispersion of the sclerosing agent, or any other injected therapeutic agent. In this manner, the extent and spread of the injection can be monitored with fluoroscopy.

It can sometimes be desirable in to remove the sclerosing agent from the targeted lung region after a predetermined time. The agent may be removed by applying suction to a proximal end of the catheter, which is left in the lung after the sclerosing agent has been injected.

Either prior to or after the sclerosing agent is injected, one or more bronchial isolation devices can optionally be implanted into the bronchial lumen leading to the targeted region in order to restrict direct flow to the target region through the bronchial pathway, as described above. In this manner, the tissue is fully isolated. However, it should be appreciated that the bronchial isolation device is not required to be implanted in combination with use of the sclerosing agent.

It should be appreciated that other methods of delivering the sclerosing agent to the target location are possible. The process of sclerosing or inflaming the tissue can be painful to the patient, so it can be beneficial to mix a local anesthetic with the sclerosing agent prior to injection.

Bulking and Sclerosing Agents with Optional Bronchial Isolation Device

One potential disadvantage of the previously-described method of using a sclerosing agent is that the sclerosing agent is exposed to the target lung tissue at full strength within a relatively quick period of time. If the sclerosing agent is suctioned out after a predetermined time, the effect of the sclerosing agent ceases. It would be desirable for the sclerosing agent to be released in a more controlled manner, such as over a period of time. This can be accomplished by combining the use of a sclerosing agent with a bulking agent.

The sclerosing agent may be released in a controlled manner as follows. The sclerosing agent is mixed with a substance having properties such that the substance is absorbed by the body over time. The substance can comprise a bulking agent (such as hydrogel) that is absorbed by the body over time. In this manner, the sclerosing agent is also released slowly over time into the surrounding tissue. In addition, the bulking agent can stop flow through the collateral pathways and prevent the sclerosing agent from being displaced from the injected location by flow through the collateral pathways.

Prior to or after the combination of the bulking agent and the sclerosing agent is injected, at least one bronchial isolation device can optionally implanted in the bronchial lumen(s) leading to the targeted lung region in order to restrict direct flow to the targeted tissue through the bronchial lumen, as described above. In this manner, the tissue is fully isolated. However, it should be appreciated that the bronchial isolation device is not required to be implanted in combination with use of the substance that combines the bulking agent and the sclerosing agent.

The combination of a bulking agent and a sclerosing agent may be injected into the lungs in the same way as was described above for the bulking agent. That is, a catheter, such as a balloon catheter, can be used to inject the combination of bulking agent and sclerosing agent into the target lung region. It should be appreciated that other methods of delivering the combination of bulking and sclerosing agent to the target location are possible. The process of sclerosing or inflaming the tissue can be painful to the patient, so it can be beneficial to mix a local anesthetic with the sclerosing agent and the bulking agent prior to injection.

A number of embodiments of the invention have been described. Nevertheless, it will be understood that various modifications may be made without departing from the spirit and scope of the invention. Accordingly, other embodiments are within the scope of the following claims.

What is claimed is:

1. A method of regulating air flow for a targeted lung region comprising a segment or lobe of the lung, comprising:
   selecting a patient having a collateral pathway in the lung;
   providing a mixture formed of a sclerosing agent selected from the group consisting of tetracycline, doxycycline, and minocycline and a substance having properties such that the substance is absorbed into lung tissue over a period of time;
   reducing collateral air flow that flows through the collateral pathway between the targeted lung region and another segment or lobe of the lung by injecting the mixture into the targeted lung region such that the substance causes the sclerosing agent to be released into tissue of the target lung region over a period of time; and
   after reducing collateral flow to the targeted lung region, reducing direct air flow in a bronchus that provides direct air flow to the targeted lung region.

2. The method of claim 1, additionally comprising removing the mixture from the targeted lung region.

3. The method of claim 2, wherein the mixture is removed using suction.

4. The method of claim 1, wherein reducing direct flow comprises implanting a flow control element which allows air flow in an exhalation direction and restricts air flow in an inspiration direction.

5. The method of claim 1, wherein the substance is a bulking agent that/fills the targeted lung region or collateral pathway to thereby at least partially fill-up a volume contained in the targeted lung region or collateral pathway, and wherein said bulking agent comprises a hydrogel.

\* \* \* \* \*